United States Patent

Borland et al.

[11] Patent Number: 5,208,374
[45] Date of Patent: May 4, 1993

[54] AMINE OXIDE PROCESS

[75] Inventors: James E. Borland; Fred J. Impastato, both of Baton Rouge, La.; Kim R. Smith, Huntington, Ind.

[73] Assignee: Ethyl Corporation, Richmond, Va.

[21] Appl. No.: 949,663

[22] Filed: Sep. 23, 1992

Related U.S. Application Data

[63] Continuation-in-part of Ser. No. 706,768, May 29, 1991, abandoned, which is a continuation-in-part of Ser. No. 569,648, Aug. 20, 1990, abandoned, which is a continuation-in-part of Ser. No. 429,032, Oct. 30, 1989.

[51] Int. Cl.$^5$ ............................................. C07C 291/00
[52] U.S. Cl. ..................................... 564/298; 564/297
[58] Field of Search .................................. 564/298, 297

[56] References Cited

U.S. PATENT DOCUMENTS

| | | | |
|---|---|---|---|
| 3,776,959 | 12/1973 | Stalioraitis et al. | 564/298 |
| 4,247,480 | 1/1981 | Murata et al. | 564/298 |
| 4,970,340 | 11/1990 | Smith | 564/298 |
| 5,130,488 | 7/1992 | Smith et al. | 564/298 |

FOREIGN PATENT DOCUMENTS 0320699  6/1989  European Pat. Off. .
0401503  12/1990 European Pat. Off. .

Primary Examiner—Marianne M. Cintins
Assistant Examiner—Michael B. Hydorn
Attorney, Agent, or Firm—Patricia J. Hogan

[57] ABSTRACT

A non-aromatic tert-amine is oxidized with hydrogen peroxide at about 20°–100° C. by a carbon dioxide-accelerated high solids process in which discoloration of the amine oxide product is minimized by diluting the carbon dioxide before allowing it to contact the reaction mixture so that the entire reaction is conducted in an atmosphere composed of carbon dioxide and an amount of inert gas, such as nitrogen or air, which is at least equal in volume to the amount of carbon dioxide.

17 Claims, No Drawings

AMINE OXIDE PROCESS

CROSS-REFERENCE TO RELATED APPLICATIONS

This application is a continuation-in-part of copending application Ser. No. 706,768, filed May 29, 1991, which is a continuation-in-part of Ser. No. 569,648, filed Aug. 20, 1990, which in turn is a continuation-in-part of Ser. No. 429,032, filed Oct. 30, 1989, all of which are now abandoned.

FIELD OF INVENTION

The invention relates to amine oxides and more particularly to an improved process for preparing them.

BACKGROUND

Amine oxides are materials which are used in a variety of applications, e.g., in the treatment of fabrics and in the preparation of hair conditioners and shampoos, toothpaste, laundry detergent powders, fabric softeners, toilet soap bars, and cosmetics, as well as in other applications. They are most commonly prepared by reacting the appropriate tert-amine, generally a non-aromatic amine such as a trialkylamine, with hydrogen peroxide.

It appears that earlier amine oxide syntheses from non-aromatic amines and hydrogen peroxide were normally conducted in the absence of catalyst or other substances that could increase the reaction rate to an acceptable degree. However, it later became preferred to conduct these syntheses in a carbon dioxide atmosphere to obtain what U.S. Pat. No. 4,247,480 (Murata et al.) describes as a "catalytic effect"—a reaction rate increase which European Patent Application 0 320 694 (Bauer et al.) indicates to be more probably provided by a carbon dioxide reaction product than by carbon dioxide itself, since carbon dioxide is reactive with both water and tert-amines.

When synthesized in the conventional manner so as to be provided as dilute solutions (as in Murata et al. and Bauer et al.), the amine oxide products have the same acceptable color whether they are prepared in the presence or absence of carbon dioxide. This is not the case, however, when the amine oxides are prepared by the newer high solids processes, such as the processes of U.S. Pat. Nos. 4,970,340 (Smith) and 5,130,488 (Smith et al.). In these high solids processes, i.e., processes wherein tert-amines are reacted with hydrogen peroxide in a liquid medium which constitutes not more than 50% by weight of the reaction mixture, the amine oxides have acceptable color when they are prepared in the absence of carbon dioxide; but they are intensely colored when a carbon dioxide atmosphere is used to speed the reaction.

SUMMARY OF INVENTION

It has been found that, when an amine oxide is prepared by reacting a nonaromatic tert-amine with hydrogen peroxide at a temperature of about 20°-100° C. in a carbon dioxide atmosphere and in a liquid medium that constitutes not more than 50% of the weight of the reaction mixture, discoloration of the product can be minimized by diluting the carbon dioxide before allowing it to contact the reaction mixture so that the entire reaction is conducted in an atmosphere composed of carbon dioxide and an amount of inert gas at least equal in volume to the amount of carbon dioxide.

DETAILED DESCRIPTION

The high solids process which is modified in accordance with the present invention is one in which the amount of liquid medium employed is minimized to provide a product which is a solid or a concentrated solution. Such processes are taught in Smith, Smith et al., and Stalioraitis et al. (U.S. Pat. No. 3,776,959), the teachings of all of which are incorporated herein by reference.

In all of the high solids processes, the reaction mixture contains the water contributed by the aqueous hydrogen peroxide, as well as the water formed by the reaction; and this water may be the only liquid medium used when it is sufficient to keep the reaction mixture fluid and stirrable. However, an organic solvent and/or additional water may be used to maintain stirrability, when appropriate, as long as the total amount of liquid medium is not allowed to exceed 50% of the weight of the reaction mixture.

When an organic solvent is utilized, it may be a material which provides the product as a concentrated amine oxide solution, as in Stalioraitis et al. It is preferred, though, that it be a solvent/non-solvent, as in Smith et al., i.e., a material in which the tert-amine and amine oxide are soluble at the reaction temperatures but in which the amine oxide is insoluble at a lower temperature, usually a substantially inert ester, hydrocarbon, halohydrocarbon, or highly polar protic solvent. This solvent, when employed, is preferably used only in the amount required to maintain a stirrable reaction mixture; and it is generally added to the reaction mixture only as needed, although the total amount to be used can be included in the initial reaction mixture if desired.

Exemplary of the organic solvents that are used in these processes are the ethyl, butyl, and sec-butyl acetates, methyl propionate, methyl benzoate, toluene, heptane, N,N-dimethylformamide, and N,N-dimethylacetamide. Ethyl acetate is apt to be especially preferred.

The amine which is oxidized in the process may be any of the amines conventionally used in such processes. As is known, these amines include a variety of tert-amines corresponding to the formula RR'R"N wherein R, R', and R" are independently selected from alkyl, hydroxyalkyl, cycloalkyl, and aralkyl groups containing up to 30 carbons and any two of those groups may form a non-aromatic heterocyclic group, such as a morpholine or piperidine ring, with the nitrogen. However, they are generally tert-amines of that formula in which R, R', and R" are independently selected from primary alkyl and hydroxyalkyl groups containing 1-30 carbons.

Because of greater interest in the oxides prepared from them, the tert-amines which are apt to be preferred for use in the process are those in which R is methyl, ethyl, or hydroxyethyl; R' is a primary alkyl group containing 6-20 carbons; and R" is independently selected from methyl, ethyl, hydroxyethyl, and primary alkyl groups containing 6-20 carbons. Those which are used in the processes in which the liquid medium is water are the tert-amines in which R is methyl, ethyl, or hydroxyethyl and R' and R" are independently selected from primary alkyl groups containing 6-20 carbons.

Exemplary of the tert-amines that may be used are trimethylamine, triethylamine, N-isobutyldimethylamine, trihexylamine, N,N-dimethyl-2-ethylhexylamine, N-eicosyldimethylamine, N-isobutyl-N-triacontylmethylamine, N-benzyldimethylamine, N-ethyldibenzylamine, N,N-diisobutyl-4-t-butylbenzylamine, tri-2-hydroxyethylamine, and, more preferably, (1) the N-alkyldimethyl- and N,N-dialkylmethylamines in which the alkyl groups are hexyl, octyl, decyl, dodecyl, tetradecyl, hexadecyl, octadecyl, and/or eicosyl, (2) the corresponding amines in which the methyl groups are replaced with ethyl or hydroxyethyl groups, and (3) mixtures of such amines.

The hydrogen peroxide which is reacted with the tert-amine is generally an aqueous hydrogen peroxide having an initial concentration of 50–99%, preferably 50–70%; and the amount employed is usually at least the stoichiometric amount but not more than a 20% molar excess. Somewhat less concentrated solutions, i.e., aqueous solutions having a concentration as low as 40%, are sometimes used in the processes in which the liquid medium is water and can also be used in the processes in which the liquid medium comprises an organic solvent. However, it is more common to use an aqueous hydrogen peroxide having a concentration of about 70% in the latter type of process, since the use of such a solution is conductive to the easy formation of a final reaction mixture in which the water/amine oxide mol ratio is not higher than about 2.1/1 and therefore can obviate the need for adjusting this ratio at the end of the reaction when the process is used, as in Smith et al., to prepare solid amine oxide dihydrates or solid amine oxides in which at least some of the molecules are dihydrate molecules.

Regardless of which type of liquid medium is used, the amine oxide synthesis is conducted by (1) adding aqueous hydrogen peroxide to the stirred tert-amine, preferably at a controlled rate, in the presence of carbon dioxide and the inert gas and preferably also in the presence of a chelating agent, such as diethylenetriaminepentaacetic acid or ethylenediaminetetraacetic acid, at a temperature in the range of about 20°–100° C., and (2) maintaining the reaction temperature for 1–24 hours before cooling the reaction mixture. It is usually preferred to use a temperature of about 60°–80° C. for at least part of the reaction.

The carbon dioxide component of the atmosphere is employed in an amount sufficient to speed the reaction, generally an amount such that the portion entering the reaction mixture is at least 0.005%, preferably at least 0.01%, based on the weight of the tert-amine. There is no maximum to the utilizable amount of carbon dioxide, based on the weight of the tert-amine. However, because of the need for the atmosphere to contain a discoloration-preventing proportion of the inert gas, the volume of carbon dioxide may not be allowed to exceed the volume of inert gas used.

The inert gas which is used in conjunction with the carbon dioxide may be any gas that is inert to the other components of the reaction mixture in the sense that—when in combination with the carbon dioxide, the tert-amine, and the aqueous hydrogen peroxide—it neither reacts with any of those other components nor serves to promote the reaction of any of those components with one another. Thus, it may be, e.g., a noble gas (especially argon or helium), nitrogen, or a normally gaseous hydrocarbon, such as methane, ethane, propane, or ethylene—gases that would be expected to be inert under the reaction conditions. However, it may also be oxygen or air—gases that normally are not considered likely to be inert.

The ability of oxygen and air to remain unreactive with a tert-amine in the process of the invention is not particularly surprising, since they are known to be less potent than the hydrogen peroxide reagent. However, their also being inert in the sense of not serving to promote the reaction is quite unexpected. As taught in copending application Ser. No. 07/706,987 (Smith, Borland, and Impastato), air accelerates the tert-amine/hydrogen peroxide reaction in the absence of carbon dioxide.

Because of availability and cost considerations, the preferred inert gases are nitrogen and air.

The carbon dioxide and inert gas may be blended with one another before being fed into the reaction vessel, or they may be introduced separately when the introduction is accomplished in a manner that avoids contacting the reaction mixture with carbon dioxide that is undiluted with the inert gas, e.g., by injecting the separate gases into the vapor space above the reaction mixture. When the carbon dioxide and inert gas are preblended, the mixture may be introduced in any suitable manner, including the technique of providing the reactor with a carbon dioxide/inert gas atmosphere initially and then sealing the reactor. However, keeping the atmosphere in motion during the reaction by continuously feeding the mixture over or through the reaction mixture appears to be preferable.

As already mentioned, the amount of inert gas used is at least equal in volume to the amount of carbon dioxide, and it may constitute as much as about 99% by volume of the atmosphere. However, since the accelerating effect of using a carbon dioxide atmosphere is reduced as the inert gas/carbon dioxide ratio is increased, it is generally preferred that the inert gas be used in an amount such as to constitute 60–90%, more preferably 60–75%, of the combined volumes of inert gas and carbon dioxide.

The amine oxides which are formed as concentrated aqueous solutions by the process of the invention are normally useful per se and have the combined advantages of containing less water than amine oxides formed by conventional low solids processes and having a visually better color than amine oxides formed by high solids processes in the presence of carbon dioxide but in the absence of the inert gas.

The amine oxides which are formed as concentrated solutions in a mixture of organic solvent and water are normally recovered before being stored, shipped, or used in their final application. Since the high solids process used to synthesize them is of particular interest for the preparation of solid amine oxide dihydrates or solid amine oxides in which at least some of the molecules are dihydrate molecules, it is customary to adjust the water content of the reaction mixture at the end of the reaction, when necessary, to provide a water/amine oxide mol ratio not higher than about 2.1/1 (a ratio in the range of about 1.9–2.1/1 when a dihydrate is desired) before separating the amine oxide from the organic solvent. However, this adjustment, which could involve either distilling some water from the reaction mixture or adding water to it, is not required when the reaction mixture already contains the right amount of water to provide the desired water/amine oxide ratio whether that ratio be the ratio appropriate for the formation of a dihydrate, a lower ratio appropriate for the formation of a monohydrate, or a higher ratio.

In the high solids processes using an organic solvent, the organic solvent may be removed by distillation.

However, as indicated by the type of solvent preferred for use in the process, it is ordinarily preferred to recover the product by cooling the reaction mixture to a temperature at which the amine oxide product is no longer soluble in the solvent and thus to precipitate it. To improve the purity of the product, additional organic solvent may be added to the reaction mixture before it is cooled and/or product may be recrystallized one or more times after being first precipitated.

Regardless of the particular type of high solids process used in the process of the invention, the amine oxide product has acceptable color and, in fact, is substantially colorless. This permits the products to be used in applications, such as cosmetics, in which they could not be used if they had the intense color of the amine oxides formed by otherwise comparable processes in which the inert gas is not used to dilute the carbon dioxide.

The following examples are given to illustrate the invention and are not intended as a limitation thereof. In these examples the gas sweep is provided by continuously feeding the gas to be tested as an atmosphere into the vapor space above the reaction mixture in the reaction vessel throughout the reaction.

EXAMPLES 1-10

Charge 100 g of N-tetradecyldimethylamine and 0.5 g of diethylenetriaminepentaacetic acid to a 250 mL flask and begin the gas sweep. Stir the mixture, heat to 65° C., add 23 g of 70% aqueous hydrogen peroxide dropwise over a period of ten minutes, and then raise the temperature to 75° C. Continue stirring the reaction mixture at 75° C. until the amine conversion reaches 99% as determined by proton NMR, adding a total of 40 mL of ethyl acetate as needed during the course of the reaction to maintain a stirrable reaction mixture. After visually determining the color of the reaction mixture, pour it into 300 mL of ethyl acetate and cool the resulting solution to 10° C. to precipitate crystalline N-tetradecyldimethylamine oxide dihydrate. Recover the dihydrate by filtration and visually determine its color.

The results obtained by using different gaseous atmospheres are shown in the table below, in which (1) gas ratios are volume ratios, (2) reaction times are the hours required to reach 99% conversion, (3) Color 1 denotes the color of the reaction mixture before it is poured into 300 mL of ethyl acetate, (4) Color 2 denotes the color of the recovered crystalline dihydrate, and (5) an intense orange color is represented by O, pale yellow by Y, and white by W.

TABLE

| Example | Atmosphere | Reaction Time | Color 1 | Color 2 |
|---------|------------|---------------|---------|---------|
| 1 | $CO_2$ | 2 | O | O |
| 2 | $CO_2/N_2$ (60/40) | 2 | O | O |
| 3 | $CO_2/N_2$ (40/60) | 3 | Y | W |
| 4 | $CO_2/N_2$ (30/70) | 3 | Y | W |
| 5 | $CO_2$/air (30/70) | 3.5 | Y | W |
| 6 | $CO_2/N_2$ (25/75) | 4 | Y | W |
| 7 | $CO_2/N_2$ (20/80) | 4 | Y | W |
| 8 | $CO_2/N_2$ (5/95) | 9 | Y | W |
| 9 | $CO_2/N_2$ (0.5/99.5) | >24 | Y | W |
| 10 | air | 8 | W | W |

What is claimed is:

1. In a process for preparing an amine oxide by reacting a non-aromatic tertamine with hydrogen peroxide at a temperature of about 20°-100° C. in a carbon dioxide atmosphere and in a liquid medium that constitutes not more than 50% of the weight of the reaction mixture, the improvement which comprises minimizing discoloration of the product by diluting the carbon dioxide before allowing it to contact the reaction mixture so that the entire reaction is conducted in an atmosphere composed of carbon dioxide and an amount of inert gas at least equal in volume to the amount of carbon dioxide.

2. The process of claim 1 wherein the inert gas is a noble gas, nitrogen, a normally gaseous hydrocarbon, oxygen, or air.

3. The process of claim 2 wherein the inert gas is nitrogen.

4. The process of claim 2 wherein the inert gas is air.

5. The process of claim 1 wherein the amount of inert gas is such as to constitute 60-90% of the combined volumes of inert gas and carbon dioxide.

6. The process of claim 5 wherein the amount of inert gas is such as to constitute 60-75% of the combined volumes of inert gas and carbon dioxide.

7. The process of claim 1 wherein the hydrogen peroxide is an aqueous solution having a concentration of at least 50% by weight.

8. The process of claim 7 wherein the liquid medium comprises an organic solvent in which the tert-amine and amine oxide are soluble at the reaction temperature but in which the amine oxide is insoluble at a lower temperature.

9. The process of claim 8 wherein the water content of the reaction mixture at the end of the reaction is adjusted, if necessary, to provide a water/amine oxide mol ratio not higher than about 2.1/1, and the reaction mixture is then cooled to precipitate the amine oxide.

10. The process of claim 8 wherein the tert-amine is a compound corresponding to the formula RR'R"N in which R,R', and R" are independently selected from primary alkyl and hydroxyalkyl groups containing 1-30 carbons.

11. The process of claim 10 wherein R is methyl, ethyl, or hydroxyethyl; R' is a primary alkyl group containing 6-20 carbons; and R" is independently selected from methyl, ethyl, hydroxyethyl, and primary alkyl groups containing 6-20 carbons.

12. The process of claim 11 wherein the atmosphere in which the reaction is conducted is a nitrogen/carbon dioxide atmosphere having a nitrogen content of 60-75% by volume.

13. The process of claim 11 wherein the atmosphere in which the reaction is conducted is an air/carbon dioxide atmosphere having an air content of 60-75% by volume.

14. The process of claim 7 wherein the liquid medium is water.

15. The process of claim 14 wherein the tert-amine is a compound corresponding to the formula RR'R"N in which R is methyl, ethyl, or hydroxyethyl and R' and R" are independently selected from primary alkyl groups containing 6-20 carbons.

16. The process of claim 15 wherein the atmosphere in which the reaction is conducted is a nitrogen/carbon dioxide atmosphere having a nitrogen content of 60-75% by volume.

17. The process of claim 15 wherein the atmosphere in which the reaction is conducted is an air/carbon dioxide atmosphere having an air content of 60-75% by volume.

* * * * *